US012589185B2

(12) United States Patent
Martin

(10) Patent No.: US 12,589,185 B2
(45) Date of Patent: Mar. 31, 2026

(54) BONE GRAFT SUBSTITUTES

(71) Applicant: ZOAN NUAIL TEORANTA, Galway (IE)

(72) Inventor: James Martin, Galway (IE)

(73) Assignee: ZOAN NUAIL TEORANTA, Galway (IE)

( * ) Notice: Subject to any disclaimer, the term of this patent is extended or adjusted under 35 U.S.C. 154(b) by 558 days.

(21) Appl. No.: 18/007,660

(22) PCT Filed: Jun. 2, 2021

(86) PCT No.: PCT/EP2021/064889
§ 371 (c)(1),
(2) Date: Dec. 1, 2022

(87) PCT Pub. No.: WO2021/245182
PCT Pub. Date: Dec. 9, 2021

(65) Prior Publication Data
US 2023/0263939 A1 Aug. 24, 2023

(30) Foreign Application Priority Data
Jun. 3, 2020 (GB) ..................................... 2008372

(51) Int. Cl.
| | |
|---|---|
| *A61L 27/36* | (2006.01) |
| *A61L 27/12* | (2006.01) |
| *A61L 27/56* | (2006.01) |
| *C12N 5/07* | (2010.01) |

(52) U.S. Cl.
CPC ........... *A61L 27/3604* (2013.01); *A61L 27/12* (2013.01); *A61L 27/365* (2013.01); *A61L 27/3687* (2013.01); *A61L 27/56* (2013.01); *C12N 5/0601* (2013.01)

(58) Field of Classification Search
None
See application file for complete search history.

(56) References Cited

FOREIGN PATENT DOCUMENTS

| | | |
|---|---|---|
| CN | 205658207 U | 10/2016 |
| EP | 2 618 858 A1 | 7/2013 |

OTHER PUBLICATIONS

Zhang et al., Journal of Crystal Growth, 343, 2012, pp. 62-67.*
Interantional Search Report and Written Opinion of PCT/EP2021/064889 mailed Sep. 16, 2021; 11 pages.
Patents Act 1977: Search Report under Section 17(5) of Application No. GB2008372.1 dated Dec. 2, 2020; 4 pages.
M.M. Hoog Antink et al., "Porous ceramics with tailored pore size and morphology as substrates for coral larval Settlement", Ceramics International, vol. 44, No. 14, Jun. 15, 2018, pp. 16561-1657; 10.1016/J.CERAMINT.2018.06.078.
Cohen et al., "Morphological and compositional changes in the skeletons of new coral recruits reared in acidified seawater: Insights into the biomineralization response to ocean acidification", Geochem. Geophys. Geosyst., vol. 10, No. 7, Jul. 24, 2009, Q07005, doi:10.1029/2009GC002411.
Combes et al., "Preparation, physical-chemical characterisation and cytocompatibility of calcium carbonate cements", Biomaterials, vol. 27, No. 9, Mar. 1, 2006, pp. 1945-1954, XP027951405.
Green et al., "Natural and Synthetic Coral Biomineralization for Human Bone Revitalization", Trends in Biotechnology, vol. 35(1), Jan. 2017, pp. 43-54; Doi: https://doi. org/10.1016/j.tibtech.2016.10. 003.
Karin Hing, "Bioceramic Bone Graft Substitutes: Influence of Porosity and Chemistry", International Journal of Applied Ceramic Technology, vol. 2, No. 3, May 1, 2005, pp. 184-199; 10.1111/j.1744-7402.2005.02020. x.
Osinga et al., "The Biology and Economics of Coral Growth", Marine Biotechnology, vol. 13(4), 2011, pp. 658-671; DOI 10.1007/s10126-011-9382-7.

* cited by examiner

*Primary Examiner* — Michael V Meller
(74) *Attorney, Agent, or Firm* — Marian E. Fundytus; Amster Rothstein & Ebenstein LLP

(57) ABSTRACT
The present invention provides a method of manufacturing a coral scaffold for use as a bone graft substitute. The method comprises growing coral in a growth medium having a carbonate hardness, dKH, of 10 or more; removing at least a portion of the coral from the growth medium; devitalising coral removed from the growth medium and sizing the devitalised coral to form the coral scaffold.

7 Claims, No Drawings

BONE GRAFT SUBSTITUTES

BACKGROUND

The present disclosure relates to a method for manufacturing a coral scaffold for use as a bone graft substitute. The present invention also relates to a bone graft substitute.

Bone graft substitutes are porous materials that provide an osteoconductive scaffold for the growth of bone-forming tissues. Various synthetic bone graft substitutes are known. Examples include ceramic products based on calcium phosphate, such as hydroxyapatite and tricalcium phosphate. Ceramic bone graft substitutes are commercially available under the trademark ProOsteon®. Natural coral has also been described for use as a bone graft substitute.

DETAILED DESCRIPTION

According to a first aspect, the present invention provides a method of manufacturing a coral scaffold for use as a bone graft substitute. The method comprises growing coral in a growth medium having a carbonate hardness, dKH, of 10 or more; removing at least a portion of the coral from the growth medium; devitalising coral removed from the growth medium and sizing the devitalised coral to form the coral scaffold.

Provided herein is a bone graft substitute comprising a coral scaffold, wherein the coral scaffold is obtainable by a method described in the present disclosure.

In the method of the present invention, coral is grown in a growth medium having a carbonate hardness, dKH, of 10 or more. By controlling the carbonate hardness at such elevated levels, it has been found that the porosity of the coral can be varied. As well as porosity, the pore size distribution and/or the pore structure may also be altered. This may allow the mechanical properties of the coral to controlled.

For example, the porosity in the coral scaffold can be varied to improve the properties of the bone graft substitute. In some instances, changes (e.g. decreases) in porosity may improve the mechanical strength of the bone graft substitute. This, in turn, may allow the material to be used in a broader range of applications, for example, where improved load bearing may be required. In some instances, changes (e.g. increases) in porosity may also improve the permeability of the bone graft substitute, improving the amount of bone ingrowth into the scaffold. Porosity may also be varied (e.g. increased) to provide greater space for nutrient and oxygen supply, and further vascularization in newly formed bone tissue. In some examples, a change in overall porosity may result in changes in the way in the bone graft substitute is resorbed by the body.

Preferably, the growth medium has a carbonate hardness, dKH, of 10 or 10.5 to 14, for example, 12 to 14. More preferably, the growth medium has a carbonate hardness, dKH, of 13 or greater, for example, 13 to 14 or about 13.5. The carbonate hardness may be controlled at a dKH of 10 to 14, preferably 12 to 14. In some examples, the method further comprises the step of controlling the carbonate hardness to within ±3 dKH units. In some examples, the carbonate hardness may be controlled to within ±2 dKH units, preferably to within ±1.5 dKH units or ±1 dKH units. More preferably, the carbonate hardness may be controlled within ±0.5 dKH units.

The coral scaffold may comprise pores that are 1 to 800 microns in size. The coral scaffold may have a heterogeneous pore size. In some examples, the coral scaffold may comprise pores that are 100 to 500 microns in size, preferably 100 to 325 microns in size. The coral scaffold may have pores with suitable sizes to facilitate cell adhesion, aggregation and proliferation, while at the same time providing sufficient space for vascularization for adequate nutrient and oxygen supply. The pore size may be selected so that the coral scaffold may be suitable for use as a bone engineering scaffold. The pore size and/or pore distribution may also be selected for improved mechanical strength.

Preferably, the coral scaffold comprises calcium carbonate. The coral scaffold may comprise at least 85 weight %, preferably at least 90 weight %, more preferably at least 95 weight % calcium carbonate. In some examples, the coral scaffold comprises at least 98 weight %, preferably at least 99 weight % calcium carbonate. The coral scaffold may consist essentially of calcium carbonate.

In some examples, at least 95 weight % of the calcium carbonate is present in the aragonite crystalline phase. In some examples, at least 99 weight % of the calcium carbonate is present in the aragonite crystalline phase. For instance, at least 99.5 weight % or at least 99.7 weight % of the calcium carbonate may be present in the aragonite crystalline phase. Crystallinity of the calcium phase may be important, as higher levels of crystallinity may improve the degradability of the bone graft substitute in vivo.

In some examples, the coral scaffold may comprise at least 85 weight %, preferably at least 90 weight %, more preferably at least 95 weight % calcium carbonate and at least 95 weight % of the calcium carbonate is present in the aragonite crystalline phase. Preferably, the coral scaffold comprises at least 98 weight %, preferably at least 99 weight % calcium carbonate and at least 99 weight % of the calcium carbonate is present in the aragonite crystalline phase. For instance, at least 99.5 weight % or at least 99.7 weight % of the calcium carbonate may be present in the aragonite crystalline phase.

The coral scaffold may be resorbable in vivo.

The method of the present invention may, in some instances, further comprise treating the coral scaffold to convert at least part of the coral scaffold to hydroxyapatite. The bone graft substitute, therefore, may be formed of a coral scaffold that comprises or consists essentially of hydroxyapatite.

In the method of the present invention, the devitalised coral may be sized in any suitable manner to form the coral scaffold. For example, the devitalised coral may be ground into a powder or broken into pieces or granules. Alternatively, the devitalised coral may be cut into wedges or blocks to form the bone graft substitute. The bone graft substituted may be an osteoconductive matrix, an osteoconductive scaffold and a bone void filler.

Growth Medium

As described above, the method of the present invention comprises growing coral in a growth medium. The coral may be a calcifying species of coral. Any suitable genera or species of coral may be grown. Examples of suitable genera include *Pocillopora, Montipora, Favites, Favia, Porites, Goniastrea, Acanthestrea, Acropora, Alvepora, Fungia, Galaxea, Hydnophora, Millepora, Seriatopora, Stylophora* and/or any coral of the order *Scleractinia*. For example, suitable species include *Pocillopora damicornis* and *Montipora digitata*. Preferably, species that can be grown in captivity in a mesocosm are selected.

The coral may be grown in any suitable growth medium. The growth medium may be an aqueous medium. The aqueous medium may be a saline solution. Examples of suitable growth media include freshwater, seawater and mixtures thereof. In some examples, a mixture of seawater and freshwater may be employed. In other examples, the growth medium may comprise a saline solution formed by dissolving sodium chloride and, optionally, other salts in water. The water may be filtered prior to use. In some examples, the growth medium may be circulated or agitated. This circulation or agitation may simulate the circulation of water that coral may be exposed to in its natural environment.

In some examples, the salinity of the growth medium may be controlled. Salinity levels may be varied depending on, for example, the species of coral grown. In some examples, the salinity may be controlled by varying the relative amounts of saltwater (e.g. seawater) and freshwater in the growth medium. Salinity may be controlled such that the specific gravity of the growth medium is from 1.0 to 1.1, preferably from 1.022 to 1.032 at 25 degrees C. In some examples, the salinity may be controlled from 1.024 to 1.026 at 25 degrees C., for instance, at about 1.025. In some examples, the method comprises controlling salinity within ±10%, for example, ±8%, ±6%, ±5%, ±4%, ±3%, ±2%, ±1%, ±0.5% of a target specific gravity value. The target specific gravity may be 1, for example, 1.02 or 1.03.

In the method of the present invention, the growth medium has a carbonate hardness, dKH, of 10 or more. Carbonate hardness is a measure of the water hardness caused by the presence of carbonate $(CO^{2-})_3$ and bicarbonate $(HCO^-)_3$ ions. The carbonate hardness is indicative of the extent to which the growth medium is buffered with respect to changes in pH. By controlling the carbonate hardness, the rate and nature of coral growth can be varied. It has surprisingly been found that, at high levels of carbonate hardness, the rate of coral growth can be enhanced. It has also been found that this increased rate in coral growth affects the mechanical properties and structure of the resulting coral. For example, the resulting coral has a different porosity. The difference in porosity may result in a different (higher or lower) porosity. In some examples, the difference in porosity may result in a different pore structure and/or a different pore size distribution. In some instances, the coral may have a lower porosity and improved mechanical strength.

In some examples, the dKH may be 10, 10.5 or 12 or more, for instance, 10 or 10.5 to 14 or 12 to 14. In some examples, the dKH may be 13 or more, for example, 13 to 14 or about 13.5. Preferably, the dKH of the growth medium is controlled at 10 or more, preferably from 12 to 14, more preferably 13 to 14. For example, the dKH of the growth medium may be maintained at 10 or more for at least 6 hours, preferably, at least 12 hours or at least 18 hours. In some instances, the dKH of the growth medium may be maintained at 10 or more for at least a day, preferably at least 3 days, more preferably at least a week and yet more preferably at least a month. In preferred instances, the dKH of the growth medium may be maintained at 10 or more for at least 2 months, for example, at least 3 months. In some instances, the dKH of the growth medium may be maintained at 10 or more until the coral is collected.

In some examples, the dKH of the growth medium is controlled at a dKH value of 10 or more within ±2 dKH units. In some examples, the dKH of the growth medium is controlled at a dKH value of 10 or more within ±1.5 dKH units, preferably within ±1 dKH units or more preferably within ±0.5 dKH units.

The dKH of the growth medium may be varied by varying the amount of carbonate and/or bicarbonate in the growth medium. For example, carbonate and/or bicarbonate may be added to the growth medium to increase the dKH of the medium. In some examples, the growth medium may be dosed with a solution of carbonate and/or bicarbonate. For example, the carbonate and/or bicarbonate may be provided as an alkali metal salt, for instance, a sodium salt. In some examples, the growth medium may be dosed with a solution of sodium carbonate at intervalsto maintain the dKH of the growth medium at 10 or more. Dosing may be performed as a bulk powder or as a stock solution.

In some examples, dKH may be monitored. dKH may be measured and/or monitored by any suitable method. For example, the dKH may be measured by manual visual titration, a manual colorimetric method or using an automatic pH electrode. In some examples, thedKH may be monitored continuously during the period of coral growth.

In addition to controlling the dKH, the concentration of certain elements in the growth medium may also be controlled. For example, the growth medium may be dosed with solutions of one or more salts, for example, metal salts. Examples of suitable salts include salts of magnesium, sodium, calcium and strontium. One or more of these salts may be employed. In some instances, metal cations present in the salts may be incorporated into the structure of the growing coral and/or otherwise promote coral growth. For example, the coral may incorporate metal ions, for instance, metal ions selected from magnesium, calcium, strontium and mixtures thereof. Suitable salts include chlorides, for example, magnesium chloride, calcium chloride and strontium chloride. Other suitable salts include phosphates, for example, sodium phosphate. In some instances, anions present in the salts may be incorporated into the structure of the growing coral, or otherwise promote coral growth. As an example, phosphate ions present in phosphate salts (e.g. sodium phosphate) may facilitate growth of the coral skeleton.

The growth medium may also be dosed with, for example, iodine. The coral may use iodine for the synthesis of pigments, which may allow them to adapt to varying light conditions and provide their tissue with protection from UV radiation. The amount of iodine in the growth medium may be controlled within prescribed limits.

In some examples, it may be possible to dose iron salts in the growth medium. It has been found, however, that, in some circumstances, iron can increase the rate of nitrification.

The amount of salt(s) and other additives added to the growth medium may be controlled within narrow limits. Accordingly, solutions of the salts/additives may be dosed at predetermined amounts into the growth medium.

In some examples, the concentration of calcium salts (e.g. calcium chloride) may be controlled in the growth medium in an amount of 200 to 500 mg/l, preferably, 350 to 450 mg/l.

In some examples, the concentration of strontium salt (e.g. strontium chloride) may be controlled in the growth medium in an amount of 0 to 12 mg/l, preferably, 6 to 9 mg/l.

In some examples, the concentration of iodine may be controlled in the growth medium in an amount of 25 to 250 mg/l, preferably, 100 to 200 g/l.

In some examples, the amount of phosphate (e.g. sodium phosphate) may be controlled from 0 to 3 mg/l, for example, 0.001 to 1 mg/l.

In some examples, the amount of iron may be controlled from 0 to 3000 mg/l. Preferably, iron concentrations are limited to below 5 mg/l, preferably, below 1 mg/l. More preferably, no iron is added to the growth medium.

The growth medium may also be dosed with ammonium salts. For example, ammonium chloride may be used. Coral has a symbiotic relationship with a dinoflagellate algae of the genus *Symbiodinium*. This symbiosis is based on mutual nutrient exploitation, with corals providing shelter and inorganic nutrients to their algal partners, while *Symbiodinium* supply their coral hosts with photosynthates that can meet at least part of the corals' energy requirements. By maintaining ammonium levels in the growth medium, it is possible to support algal growth, which, in turn, facilitates the growth of the coral. In some examples, ammonium levels are maintained at a concentration of 0 to 1.5 ppm, preferably about 0.5 ppm. Ammonium levels may be maintained by dosing ammonium salts into the growth medium e.g. periodically or continuously. Ammonium levels may be maintained at about 0.5 ppm for e.g. a day. Dosing may be carried out as a bulk powder or as a stock solution.

Where dosing solutions are added to the growth medium, dosing may be carried out manually e.g. at periodic intervals during the growth of the coral. Alternatively, dosing may be carried out automatically e.g. using a peristaltic pump. Dosing may be carried out using a stock solution.

In some instances, live rock may be placed in the growth medium. Coral may anchor to the rock. The rock may also provide a site for nitrifying bacteria within the mesocosm.

The growth medium may be cycled prior to use to ensure that it is stable with nitrifying bacteria. Cycling may be performed according to methods that are well-known in the art.

During the period of coral growth, the temperature of the growth medium may be controlled. Suitable temperatures range from 10 to 32 degrees C., preferably 19 to 32 degrees C. Preferably, the temperatures are controlled within 20 to 27 degrees C., more preferably at about 25 degrees C.

The growth medium may also be subjected to a controlled amount of light on a predetermined cycle as required. The growth medium may be irradiated with light for 4 to 20 hours a day, for example, 6 to 15 hours a day, preferably 8 to 12 hours a day.

It may take at least one month, for example, two to six months before the coral is ready for harvesting/collection. In some instances, it may take three to four months before the coral is ready for harvesting. In some examples, the coral may be considered to be ready for harvesting once it reaches at least 150%, preferably, at least 180% or at least 200% of its original volume.

Once ready for harvest, the coral may be collected using known methods.

Devitalising Coral

The collected coral may be devitalised using any suitable method. For example, the coral may be devitalised by treatment with an oxidizing agent, for instance, hypochlorite (e.g. sodium hypochlorite). In one example, the coral may be treated with a solution of hypochlorite for a predetermined length of time. Suitable time periods range from 3 to 50 hours, for example, 5 to 40 hours. If required, the devitalised coral may then be rinsed with water (e.g. deionized water). The collected coral may be dried. Drying may be performed at elevated temperatures. Suitable temperatures range from 50 to 190 degrees C., for instance, 80 to 100 degrees C. In some instances, the collected coral may be subjected to depyrogenation.

The devitalised coral may then be sized using any suitable technique. For example, the devitalised coral may be ground into a powder, or broken into pieces. Where the devitalised coral is broken into pieces, the pieces may measure 0.5 to 5 mm, preferably, 1 to 2 mm across. Alternatively, the devitalised coral may be cut into blocks or wedges, depending on the nature of the bone graft substitute produced. Where the devitalised coral is sized to form particles of a coral scaffold, sizing may be carried out by crushing or milling. Any suitable crushing or milling technique may be used. For instance, the devitalised coral may be milled e.g. using a disc mill.

Other Treatments

Once sized, the devitalised coral may be used to form the coral scaffold of the bone graft substitute. In some examples, the sized coral may be used as the coral scaffold after, for example, cleaning and disinfection.

In other examples, the coral may be treated prior to use as the coral scaffold. For example, the coral may be treated to convert at least part of the calcium carbonate in the coral to hydroxyapatite. Any suitable method for converting the calcium carbonate in the coral to hydroxyapatite may be employed. For example, the calcium carbonate may be treated by hydrothermal treatment to produce hydroxyapatite. In some examples, the coral may be treated with phosphoric acid ($H_3PO_4$) a dihydrogen phosphate salt (e.g. ammonium dihydrogenphosphate, $NH_4H_2PO_4$) to produce hydroxyapatite. The reaction may occur in the presence of water and at elevated temperatures. Suitable temperatures range from, for example, 160 to 220 degrees C. Suitable pressures range from 6 to 10 MPa, for example, 8 MPa. While the conversion of calcium carbonate to hydroxyapatite may be useful for certain applications, for other applications, it may be preferable for the calcium carbonate to remain unconverted. In some examples, coral scaffolds comprising calcium carbonate may be preferable for use in the manufacture of resorbable bone grafts. In some examples, the coral scaffold is used without treating the scaffold to convert the calcium carbonate to hydroxyapatite.

Porosity

The coral scaffold may have a porosity of at least 15%, for example, at least 18% or at least 20%. In some examples, the porosity may be at least 21°A, at least 25%, at least 30%, at least 40%, at least 50%, or at least 60%. In some examples, the coral scaffold may have a porosity of at least 70%, at least 75%, and at least 80%. In some examples, the coral scaffold may have a porosity of at least 85%, at least 90%. The coral scaffold may have a porosity of up to 98%, for example, up to 95%. In some instances, the coral scaffold may have a porosity of 15 to 98%, 18 to 80%, 20 to 70% or 21 to 60%. In some examples, the coral scaffold may have a porosity of 70 to 95%, for example, 75 to 90% or 80 to 85%. These porosities may reflect the volume porosity of the coral scaffold. For instance, where the coral scaffold takes the form of an individual unit (e.g. wedge or block), the porosity may be indicative of the volume or pores within the unit (e.g. wedge of block). Similarly, where the coral scaffold takes the form of particles, the porosity may be indicative of the volume of the pores within each particle of the coral scaffold. This total pore volume may reflect the total pore volume of the devitalised coral. This total pore volume may reflect the "internal" pore volume of the coral scaffold. Alternatively, the porosities may also reflect the porosity of voids between individual particles of the coral scaffold. For example, where the coral scaffold comprises particles, the volume porosity may include the volume of pores within each particle and the volume of the voids formed between particles.

In some examples, the coral scaffold comprises particles. The porosity of the coral scaffold particles may be at least 15%, for example, at least 18% or at least 20%. In some examples, the porosity may be at least 21%, for example, at least 25%, at least 30%, at least 40%, at least 50%, or at least 60%. In some examples, the coral scaffold particles may have a porosity of least 70%, preferably at least 75%, and yet more preferably at least 80%. In some examples, the coral scaffold particles may have a porosity of at least 85%, preferably 90%. The coral scaffold particles may have a porosity of up to 98%, preferably up to 95%. In some instances, the coral scaffold particles may have a porosity of 15 to 98%, 18 to 80%, 20 to 70% or 21 to 60%. In some instances, the coral scaffold particles may have a porosity of 70 to 95%, for example, 75 to 90% or 80 to 85%. These porosities may reflect the porosity within each individual particle, or the porosity within each individual particle and the void volume before the particles.

As discussed above, the porosity of the coral scaffold is a relevant parameter with respect to its application as a bone graft substitute. In some instances, porosity can affect bone growth into the grafted area and, thus, graft integration and healing. By carrying porosity (e.g. increasing porosity) of the coral scaffold, the permeability of the bone graft substitute may be improved. This may improve the amount of bone ingrowth into the scaffold. Varying (e.g. increasing) porosity may also provide greater space for nutrient and oxygen supply, and further vascularization in newly formed bone tissue. In some instances, varying porosity (e.g. decreasing porosity) may also result in a resorbable structure that can be tailored to suit requirements.

Porosity may be measured by any suitable method.

In some examples, the porosity of the sample may be measured by mercury porosimetry. Mercury porosimetry may be used to measure the porosity within the coral scaffold. Mercury porosimetry is used to measure the porosity of a material by applying controlled pressure to a sample immersed in mercury. External pressure is required for mercury to penetrate into the pores of a material due to high contact angle of mercury. The amount of pressure required to intrude into the pores is inversely proportional to the size of the pores. The larger the pore the smaller the pressure needed to penetrate into the pore. A mercury porosimeter can generate volume and pore size distributions from the pressure versus 15 intrusion data generated by the instrument using the Washburn equation. A mercury porosimeter can also be used to provide the total pore size area of a sample. Mercury porosimetry may be useful for determining the porosity of the coral scaffold, for instance, within individual particles of the coral scaffold.

The porosity of the coral scaffold may be determined using known methods described in e.g. ISO 23145-1:2007 or ASTM UOP 578-11. In one example, the porosity may be measured by inserting a volume of the coral scaffold into a test container having a known volume. The test container may be tapped several times (e.g. 1000 times) using, for example, a pneumatic device to ensure that the coral scaffold settles into the test container. Excess coral scaffold can be removed from the top of the container to ensure that the container is filled. By dividing the mass of the filled container by the known volume of the container, the tapped density, ρ tapped, may be obtained. The porosity (volume porosity), P, may be calculated from the tapped density as follows:

$$P=[1-(\rho tapped/\rho theoretical)]\times 100$$

where ρ theoretical is the theoretical density of the coral scaffold material (e.g. aragonite, ρ theoretical=2.93 g/cm$^3$).

This porosity determined from the tapped and theoretical densities may be indicative of the porosity within and between the particles of the coral scaffold.

The coral scaffold may comprise pores that are 1 to 800 microns in size. The coral scaffold may have a heterogeneous pore size. In some examples, the coral scaffold may comprise pores that are 100 to 500 microns in size, preferably 100 to 325 microns in size. The coral scaffold may have pores with suitable sizes to facilitate cell adhesion, aggregation and proliferation, while at the same time providing sufficient space for vascularization for adequate nutrient and oxygen supply. The pores may be formed within the structure of the coral rather than between individual particles of the coral scaffold.

The coral scaffold may have a bulk density of at least 1.9 g/cm$^3$, for example, 2.00 to 2.20 g/cm$^3$, preferably 2.02 to 2.18 g/cm$^3$.

Calcium and Calcium Carbonate Content

The coral scaffold may have a calcium content of greater than at least 35 weight %, preferably at least 37 weight %. In some examples, the coral scaffold may contain 35 to 45 weight % calcium, preferably 37 to 40 weight % calcium.

Preferably, the coral scaffold comprises calcium carbonate. The coral scaffold may comprise at least 85 weight %, preferably at least 90 weight %, more preferably at least 95 weight % calcium carbonate. In some examples, the coral scaffold comprises at least 98 weight %, preferably at least 99 weight % calcium carbonate. The coral scaffold may consist essentially of calcium carbonate.

In some examples, at least 95 weight % of the calcium carbonate is present in the aragonite crystalline phase. In some examples, at least 99 weight % of the calcium carbonate is present in the aragonite crystalline phase. For instance, at least 99.5 weight % or at least 99.7 weight % of the calcium carbonate may be present in the aragonite crystalline phase. In some examples, a small amount of calcite may be present. For example, calcite may form up to 1 weight %, preferably up to 0.5 weight %, more preferably up to 0.3 weight % of the calcium carbonate present in the coral scaffold. In some instances, the calcium carbonate consists essentially of calcium carbonate present in the aragonite and/or calcite phase. Crystallinity of the calcium phase may be important, as higher levels of crystallinity may improve the degradability of the bone graft substitute in vivo. Phase quantification may be carried out using any suitable method, for example, by X-ray diffraction as outline in, for instance, ISO 13779-3:2018.

In some examples, the coral scaffold may comprise at least 85 weight %, preferably at least 90 weight %, more preferably at least 95 weight % calcium carbonate and at least 95 weight % of the calcium carbonate is present in the aragonite crystalline phase. Preferably, the coral scaffold comprises at least 98 weight %, preferably at least 99 weight % calcium carbonate and at least 99 weight % of the calcium carbonate is present in the aragonite crystalline phase. For instance, at least 99.5 weight % or at least 99.7 weight % of the calcium carbonate may be present in the aragonite crystalline phase.

In addition to calcium, other metals may be present in the coral scaffold. For example, the coral scaffold may comprise sodium, magnesium and/or strontium. Where magnesium is present, magnesium may be present in an amount of up to 2000 mg/kg, for instance, 1000 to 1500 mg/kg, preferably 1100 to 1300 mg/kg. Where sodium is present, sodium may be present in an amount of up to 8000 mg/kg, for example, 4000 to 7000 mg/kg, preferably 5000 to 6000 mg/kg. Where strontium is present, strontium may be present in an amount of up to 9000 mg/kg, for example, 65000 to 8500 mg/kg or 7000 to 8000 mg/kg.

As mentioned above, the coral scaffold is resorbable in vivo. When the coral scaffold is dissolved in e.g. a TRIS (trisaminomethane) buffer solution, the pH of the resulting solution is substantially unchanged even after 24, 48 or 72 hours. The maximum deviation from the initial pH value may be less than 0.3, preferably less than 0.2.

Bone Graft Substitute

The coral scaffold may be sized using any suitable method to provide the bone graft substitute. For example, the coral scaffold may be ground into a powder or particles for use as the bone graft substitute. Alternatively, the coral scaffold may be cut into blocks or wedges as required for use as a bone graft substitute. The size and shape employed may depend on the would requiring treatment.

In some examples, the coral scaffold may be sized as particles or "granules". The particles may have a particle size of 0.1 to 5 mm, for example, 0.5 to 3 mm. Preferably, the particle size may be 1 to 2 mm. In some examples, at least 70 weight %, more preferably at least 80 weight % or at least 90 weight % of the particles may have a particle size of from 1 to 2 mm.

The coral scaffold may form a bone graft substitute for use as an osteoconductive matrix. In some examples, the coral scaffold may be used as an osteoconductive matrix for cancellous bone tissue.

The coral scaffold may be used as bone graft substitute for use as a bone void filler. Such a substitute may be used to fill gaps and voids in bone, for example, those caused by trauma or disease. Such bone graft substitutes may be injectable and/or moldable to conform to the wound site.

The bone graft substitute may be suitable for promoting soft tissue in growth, for instance, collagen in-growth.

The bone graft substitute may have a porosity of at least 15%, for example, at least 18% or at least 20%. In some examples, the porosity may be at least 21%, at least 25%, at least 30%, at least 40%, at least 50%, or at least 60%. In some examples, the bone graft substitute may have a porosity of at least 70%, preferably at least 75%, and yet more preferably at least 80%. In some examples, the bone graft substitute may have a porosity of at least 85%, preferably 90%. The bone graft substitute may have a porosity of up to 98%, preferably up to 95%. In some instances, the bone graft substitute may have a porosity of 15 to 98%, 18 to 80%, 20 to 70% or 21 to 60%. In some instances, the bone graft substitute may have a porosity of 70 to 95%, for example, 75 to 90% or 80 to 85%.

These porosities may reflect the volume porosity of the bone graft substitute. For instance, where the bone graft substitute takes the form of an individual unit (e.g. wedge or block), the porosity may be indicative of the volume or pores within the unit (e.g. wedge or block). Similarly, where the bone graft substitute takes the form of particles, the porosity may be indicative of the volume of the pores within each particle of the bone graft substitute. This total pore volume may reflect the total pore volume of the devitalised coral. This total pore volume may reflect the "internal" pore volume of the bone graft substitute. Alternatively, the porosities may also reflect the porosity of voids between individual particles between particles of the bone graft substitute. For example, where the bone graft substitute comprises particles, the volume porosity may include the volume of pores within each particle and the volume of the voids formed between particles. Preferably, the total pore volume reflects the "internal" pore volume of the bone graft substitute. Accordingly, where the bone graft substitute takes the form of particles, the porosity is indicative of the volume of the pores within each particle of the bone graft substitute.

In some examples, the bone graft substitute comprises particles. The porosity of the bone graft substitute particles may be at least 15%, for example, at least 18% or at least 20%. In some examples, the porosity may be at least 21%, at least 25%, at least 30%, at least 40%, at least 50%, or at least 60%. The porosity of the bone graft substitute particles may be at least 70%, preferably at least 75%, and yet more preferably at least 80%. In some examples, the bone graft substitute particles may have a porosity of at least 85%, preferably 90%. The bone graft substitute particles may have a porosity of up to 98%, preferably up to 95%. In some instances, the bone graft substitute particles may have a porosity of 15 to 98%, 18 to 80%, 20 to 70% or 21 to 60%. In some instances, the bone graft substitute particles may have a porosity of 70 to 95%, for example, 75 to 90% or 80 to 85%. These porosities may reflect the porosity within each individual particle, or the porosity within each individual particle and the void volume before the particles.

As discussed above, the porosity of the bone graft substitute is a relevant parameter for bioengineering applications. In some instances, porosity can affect bone growth into the grafted area and, thus, graft integration and healing. The porosity in the bone graft substitute can affect the permeability, affecting the amount of bone ingrowth. The porosity may also provide adequate space for nutrient and oxygen supply, and further vascularization in newly formed bone tissue. The porosity may also influence the mechanical strength of the bone graft substitute.

Porosity may be measured by any suitable method, including methods that are known in the art and those methods discussed above in relation to the coral scaffold.

The bone graft substitute may comprise pores that are 1 to 800 microns in size. The coral scaffold may have a heterogeneous pore size. In some examples, the bone graft substitute may comprise pores that are 100 to 500 microns in size, preferably 100 to 325 microns in size. The bone graft substitute may have pores with suitable sizes to facilitate cell adhesion, aggregation and proliferation, while at the same time providing sufficient space for vascularization for adequate nutrient and oxygen supply. The pores may be formed within the structure of the coral rather than between individual particles of the bone graft substitute.

The bone graft substitute may have a bulk density of at least 1.9 $g/cm^3$, for example, 2.00 to 2.20 $g/cm^3$, preferably 2.02 to 2.18 $g/cm^3$.

In some examples, the bone graft substitute may be treated with a pharmaceutical composition, protein, growth factor or cells (e.g. stem cells) to facilitate bone growth.

In some examples, the bone graft substitute may have a compressive strength of 1.5 to 6 MPa, for instance, 3 to 5 MPa.

Example 1

Coral of the species *Pocillopora damicornis* was grown in a growth medium comprising a mixture of seawater and freshwater. Seawater was sourced from the Atlantic ocean and filtered and brought up to temperature before use. Freshwater was treated by reverse osmosis and maintained at an appropriate temperature prior to use. The mesocosm was cycled before any livestock was added to the system.

The mesocosm was controlled as shown in Table 1 below:

| Parameter | Target set point |
| --- | --- |
| Lighting/hours | 10 |
| Temperature/° C. | 25 |
| Salinity/Specific Gravity | 1.025 |
| Carbonate hardness/dKH | 6.6 |
| Calcium/mg/l (based on weight of total salt) | 400 |
| Strontium/mg/l (based on weight of total salt) | 8 |
| iodine/mg/l | 60 |
| Iron/mg/l | 0 |
| Nitrate/mg/l | 1 |
| Phosphate/mg/l | 0.03 |

After approximately 3 months of growth, the coral had approximately doubled in volume. The coral was collected as a whole unit. The coral was then cut in half. One half was returned to the mesocosm for further growth, while the remaining half was devitalised by exposing the coral to a 5% solution of hypochlorite for 30 hours. The devitalised coral was then rinsed in deionized water for 30 hours and dried at 90 degrees C. for 2 hours.

The coral was then milled using a pestle and mortar and sieved through a stainless steel sieve to obtain particles of 1-2 mm in size. The porosity of the coral was determined using mercury porosimetry (ASTM UOP 578-11). The coral was determined to have a porosity of 23.16%. This porosity was determined to be the porosity within the coral particles and not the porosity arising from gaps between coral particles.

Example 2

The procedure of Example 1 was repeated except that the carbonate hardness was controlled at about 13.5. The collected coral was found (by observation only) to be more brittle than the collected coral grown in Example 1. However, no measurement was taken on this particular sample.

The coral was observed to grow more quickly at higher dKH.

Example 3

The procedure of Example 1 was repeated except that the carbonate hardness was controlled at about 10.0. The collected coral was determined to have a porosity of determined using mercury porosimetry (ASTM UOP 578-11). The coral was determined to have a porosity of 21.49%. This porosity was determined to be the porosity within the coral particles and not the porosity arising from gaps between coral particles.

Example 4

The procedure of Example 1 was repeated with the following coral species:

*Montipora capricornis*
*Turbinaria* sp
*Stylophora milka*
*Montipora digitata*

The porosities of the resulting corals were determined using mercury porosimetry (ASTM UOP 578-11). The results are as shown in the table below.

The procedure of Example 1 was also repeated with the above coral species but at carbonate levels of 10.0. The porosities of the resulting corals were also determined and shown in Table 1. The coral was observed to grow more quickly at the higher dKH. The decrease in porosity observed at higher dKH may be associated with the improved mechanical strength of the samples grown at higher dKH.

| Species | Porosity at 6.6 dKH | Porosity at 10.0 dKH |
| --- | --- | --- |
| *Montipora capricornis* | 67.06 | 49.14 |
| *Turbinaria sp* | 56.10 | 53.83 |
| *Stylophora milka* | 42.07 | 24.93 |
| *Montipora digitata* | 70.29 | 57.92 |

The invention claimed is:

1. A method of manufacturing a coral scaffold comprising:
   a) growing coral in a growth medium having a carbonate hardness, dKH, of 10 or more;
   b) removing at least a portion of the coral from the growth medium;
   c) devitalising the coral removed from the growth medium; and
   d) sizing the devitalised coral to form the coral scaffold.

2. The method of claim 1, wherein the carbonate hardness is dKH, of the growth medium at 10 to 14.

3. The method of claimed 2, wherein the growth medium has a carbonate hardness, dKH, of 12 to 14.

4. The method of claim 1, wherein the coral scaffold has a porosity of 20% or greater.

5. The method of claim 1, wherein the coral scaffold forms at least part of a bone graft substitute selected from the group consisting of an osteoconductive matrix, an osteoconductive scaffold and a bone void filler.

6. The method of claim 1, wherein the coral scaffold has pores that are 1 micron to 800 microns in size.

7. The method of claim 1, wherein the coral scaffold comprises calcium carbonate and at least 99 weight % of the calcium carbonate is present in the aragonite crystalline phase.

* * * * *